US00PP23192P2

(12) United States Plant Patent
Danziger

(10) Patent No.: US PP23,192 P2
(45) Date of Patent: Nov. 13, 2012

(54) ***DIASCIA* PLANT NAMED 'DGENT29'**

(50) Latin Name: *Diascia barerae*
Varietal Denomination: DGENT29

(75) Inventor: Gavriel Danziger, Moshav Mishmar Hashiva (IL)

(73) Assignee: Danziger 'DAN' Flower Farm

( * ) Notice: Subject to any disclaimer, the term of this patent is extended or adjusted under 35 U.S.C. 154(b) by 0 days.

(21) Appl. No.: 13/066,973

(22) Filed: Apr. 29, 2011

(51) Int. Cl.
*A01H 5/00* (2006.01)

(52) U.S. Cl. ..... Plt./425

(58) Field of Classification Search ..... Plt./425
See application file for complete search history.

*Primary Examiner* — Annette Para

(74) *Attorney, Agent, or Firm* — Cassandra Bright

(57) ABSTRACT

A new and distinct *Diascia* cultivar named 'DGENT29' is disclosed, characterized by deep pink flowers and abundant flowering. The new variety has a compact growth habit and good temperature tolerance range for *Diascia*. The new variety is a *Diascia*, normally produced as an outdoor garden or container plant.

2 Drawing Sheets

Latin name of the genus and species: *Diascia barerae*.
Variety denomination: 'DGENT29'.

BACKGROUND OF THE INVENTION

The new *Diascia* cultivar is a product of a planned breeding program conducted by the inventor, Gavriel Danziger, in Moshav Mishmar Hashiva, Israel. The objective of the breeding program was to produce new *Diascia* varieties for ornamental commercial applications. The cross resulting in this new variety was made during April 2008.

The seed parent is the unpatented, proprietary seedling variety referred to as *Diascia barerae* 'Di-8-1177' The pollen parent is unknown, as the crossing resulting in 'DGENT29' was an open pollination, with unidentifiable pollen parents. The new variety was discovered in March 2009 by the inventor in a group of seedlings resulting from the 2008 crossing, in a research greenhouse in Moshav Mishmar Hashiva, Israel.

Asexual reproduction of the new cultivar 'DGENT29' by vegetative cuttings was first performed at a research greenhouse in Moshav Mishmar Hashiva, Israel in April 2009 and has shown that the unique features of this cultivar are stable and reproduced true to type in successive generations.

SUMMARY OF THE INVENTION

The cultivar 'DGENT29' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGENT29' These characteristics in combination distinguish 'DGENT29' as a new and distinct *Diascia* cultivar:

1. Deep pink flower color
2. Highly floriferous
3. Compact plant habit
4. Good temperature tolerance for a *Diascia* plant Plants of the new cultivar 'DGENT29' are similar to plants of the seed parent, *Diascia barerae* 'DI-8-1177' in most horticultural characteristics, however, plants of the new cultivar 'DGENT29' produce flowers of a different color, and a less upright plant habit.

COMMERCIAL COMPARISON

Plants of the new cultivar 'DGENT29' are comparable to the variety *Diascia* 'Whisper Pumpkin', unpatented. The two *Diascia* varieties are similar in most horticultural characteristics, however, the new variety 'DGENT29' differs in having different color flowers, smaller flowers and an earlier flowering habit.

Plants of the new cultivar 'DGENT29' can also be compared to the commercial variety *Diascia* 'DALA ABLOS' U.S. Plant Pat. No. 20,934. These varieties are similar in most horticultural characteristics, however 'DGENT29' has darker pink colored flowers and an overall larger plant habit.

BRIEF DESCRIPTION OF THE PHOTOGRAPHS

Figure 1:
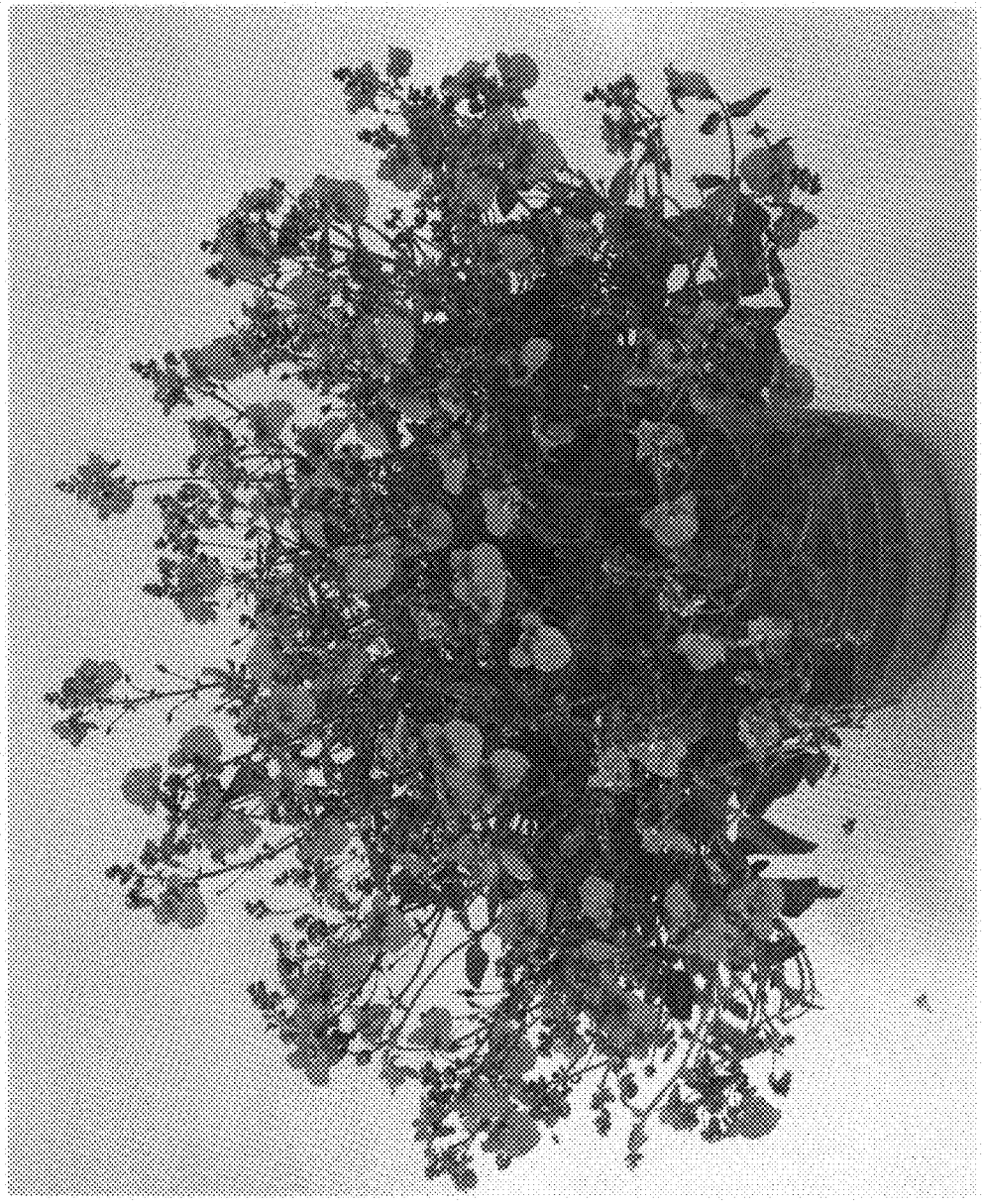

The accompanying photograph in FIG. 1 illustrates in full color a typical plant of 'DGENT29' grown in a greenhouse, in a 13 cm basket. Age of the plant photographed is approximately 3 months from a rooted cutting.

Figure 2:
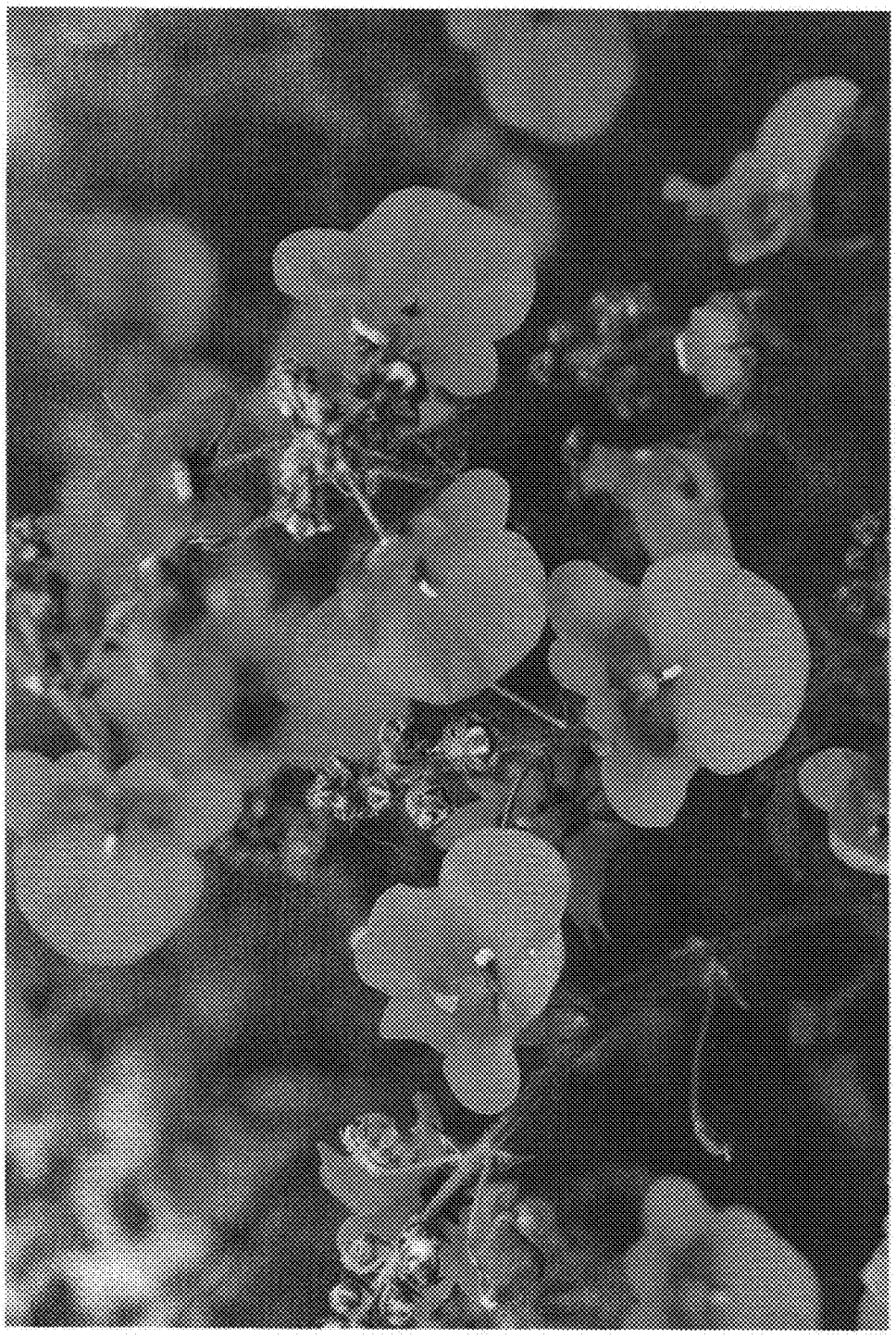

FIG. 2 illustrates in full color a close up of a typical bloom of 'DGENT29'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DGENT29' plants grown in a greenhouse, and moved outdoors during Spring in Moshav Mishmar Hashiva, Israel. The growing temperature ranged from 18° C. to 28° C. during the day and from 8° C. to 15° C. during the night. General light conditions are bright, normal sunlight. Measurements and numerical values represent averages of typical plant types. Plants are approximately 60 days old from a rooted cutting. Botanical classification: *Diascia barerae* 'DGENT29'.

PROPAGATION

Time to initiate roots: About to 8 to 14 days at approximately 20° C.
Root description: Fine, fibrous.

PLANT

Age of plant described: Approximately 60 days from a rooted cutting.
Growth habit: Compact and upright.
Height: Approximately 21 cm.
Plant spread: Approximately 50 cm.
Growth rate: Rapid.
Branching characteristics: Very well branched.
Length of lateral branches: Approximately 27 cm.
Diameter of lateral branches: Approximately 0.2 cm.
Texture of lateral branches: Smooth.
Internode length: Average 5 cm.
Strength of stem: Fragile.
Color of lateral branches: Near RHS yellow-green group 144-A.
Aspect/angle of branches: 45°.
Number of leaves per lateral branch: Approximately 6 to 8.

FOLIAGE

Leaf:
*Arrangement*.—Opposite.
*Average length*.—Approximately 2.5 cm.
*Average width*.—Approximately 1.9 cm.
*Shape of blade*.—Deltate.
*Apex*.—Acute.
*Base*.—Truncate.
*Attachment*.—Stalked.
*Margin*.—Crenate.
*Texture of top surface*.—Smooth.
*Texture of bottom surface*.—Smooth.
*Appearance top surface*.—Shiny.
*Appearance bottom surface*.—Matte.
*Color*.—Young foliage upper side: Near RHS Green 143 A. Young foliage under side: Near RHS Yellow-Green 147 C. Mature foliage upper side: Near RHS Green 137 A. Mature foliage under side: Near RHS Yellow-Green 147 C.
*Venation*.—Type: Pinnate. Venation color upper side: Near RHS Green 137 B. Venation color under side: Near RHS Yellow-Green 144 A.
*Petiole*.—Length: Average 0.6 cm. Diameter: Average 0.2 cm. Pubescence: none.
*Color*.—Near RHS Green 139 C.

FLOWER

Natural flowering season: Spring. Autumn, Winter.
Days to flowering from rooted cutting: 20.
Flower longevity on plant: 4 days.
Persistent or self-cleaning: Self-Cleaning.
Fragrance: None.
Inflorescence arrangement:
*Inflorescence height*.—3 cm.
*Inflorescence width*.—4 cm.
*Quantity of flowers per inflorescence*.—4 fully open flowers, on average.
Individual flower form: Single, zygomorphic, salver-shaped.
Flower:
*Diameter of entire flower*.—Approximately 2.4 cm.
*Length of flower*.—Approximately 2.2 cm.
Bud:
*Bud shape*.—Oblate.
*Bud length*.—Approximately 0.4 cm.
*Bud diameter*.—Approximately 0.5 cm.
*Bud color*.—Near RHS Yellow-Green 145 D.
*Opening rate, from bud to fully open*.—4 Days.
Petals:
*Quantity*.—5.
*Arrangement*.—The two small upper petals nearly entirely fused, two lateral lobes and a broad lower lobe; two short spurs emerge at the underside, formed by the lower ends of lateral and lower petals.
*Length*.—2.3 cm.
*Width*.—1.9 cm.
*Shape*.—Rounded.
*Apex*.—Cordate.
*Base*.—Truncate.
*Margin*.—Entire.
*Texture, upper and lower surfaces*.—Smooth.
*Appearance*.—Shiny.
*Color*.—When opening, upper surface: Near RHS Red-Purple N57-C. When opening, lower surface: Near RHS Red-Purple N57-C. Fully opened, upper surface: Near RHS Red-Purple 61-C. Fully opened, lower surface: Near RHS Red-Purple 61-C. Fading, upper surface: Near RHS Red-Purple 62-A. Fading, lower surface: Near RHS Red-Purple 62-A.
Peduncle:
*Peduncle length*.—Approximately 3.5 cm.
*Peduncle diameter*.—Approximately 0.2 cm.
*Angle*.—Approximately 0 deg from center of whorl.
*Color*.—Near RHS Yellow-Green 146-A.
*Peduncle texture*.—Smooth.
Pedicel:
*Pedicel length*.—Approximately 1.5 cm.
*Pedicel diameter*.—Approximately 0.1 cm.
*Angle*.—Approximately 45 deg from center of whorl.
*Color*.—Near RHS Yellow-Green 145-B.
*Pedicel texture*.—Scabrous.

REPRODUCTIVE ORGANS

Androecium:
*Stamens*.—4.
*Anther shape*.—Cleft.
*Anther length*.—Approximately 1 mm.
*Anther color*.—Near RHS Yellow 3-A.
*Pollen quantity*.—Abundant.
*Pollen color*.—Near RHS Yellow 9-A.
Gynoecium:
*Pistil number*.—1.
*Pistil shape*.—Cylindrical.
*Pistil length*.—Approx. 2.3 cm.
*Style length*.—Approx. 0.5 cm.
*Style color*.—Near RHS Green-Yellow 1-D.
*Stigma shape*.—Oval.

*Stigma color*.—Near RHS Green-Yellow 1-D.
*Ovary diameter*.—1 cm.
*Ovary color*.—Near RHS Yellow-Green 145-B.

OTHER CHARACTERISTICS

Seeds and fruits: Not observed.
Disease/pest resistance: Neither resistance nor susceptibility to pathogens and pests common to *Diascia* have been observed.
Temperature tolerance: The new variety exhibits a good temperature tolerance range for *Diascia*. Good tolerance for temperatures between −1 to 35° C.

What is claimed is:

1. A new and distinct cultivar of *Diascia* plant named 'DGENT29' as herein illustrated and described.

* * * * *